United States Patent
Baharad et al.

[11] Patent Number: 5,802,622
[45] Date of Patent: Sep. 8, 1998

[54] PROTECTIVE GOGGLES

[75] Inventors: Ram Baharad, Kfar Azar; Michael Barel, Ramat Efaal, both of Israel

[73] Assignee: Shalon Chemical Industries Ltd., Tel Aviv, Israel

[21] Appl. No.: 848,294

[22] Filed: Apr. 29, 1997

Related U.S. Application Data

[63] Continuation-in-part of Ser. No. 645,017, May 9, 1996, abandoned.

[51] Int. Cl.⁶ .......................................... A61F 9/02
[52] U.S. Cl. .......................... 2/434; 2/436; 2/443; 2/452; 2/2.5
[58] Field of Search ................. 2/426, 427, 431, 2/432, 435, 436, 437, 438, 439, 442, 443, 444, 445, 446, 447, 448, 450, 452, 2.5, 8

[56] References Cited

U.S. PATENT DOCUMENTS

| | | | |
|---|---|---|---|
| 2,504,524 | 4/1950 | Hayward | 2/452 |
| 2,615,163 | 10/1952 | Ring | 2/431 |
| 2,618,782 | 11/1952 | Christensen et al. | 2/436 |
| 3,031,675 | 5/1962 | Dubach | 2/437 |
| 3,395,406 | 8/1968 | Smith | 2/436 |
| 3,505,680 | 4/1970 | Ring | 2/435 |
| 3,591,864 | 7/1971 | Allsop | 2/436 |
| 3,931,646 | 1/1976 | Loughner | 2/452 |
| 5,341,516 | 8/1994 | Keim | 2/452 |
| 5,410,763 | 5/1995 | Bollé | 2/436 |
| 5,542,130 | 8/1996 | Grabos, Jr. et al. | 2/436 |
| 5,689,834 | 11/1997 | Wilson | 2/436 |

FOREIGN PATENT DOCUMENTS

| | | | |
|---|---|---|---|
| 1151454 | 8/1983 | Canada | 2/426 |
| 2684292 | 6/1993 | France | 2/426 |
| 94/16654 | 8/1994 | WIPO | 2/426 |

*Primary Examiner*—Michael A. Neas
*Attorney, Agent, or Firm*—Browdy and Neimark

[57] ABSTRACT

Protective goggles having a rigid, ballistically resistant transparent shield sealingly fittable over the eyes of a wearer via a resilient gasket having airing ports and a head gear for supporting the goggles. A second transparent radiation protective shield is detachably retained exterior to the ballistically resistant shield and in parallel relation thereto with impervious sealing means provided between both shields along their peripheries so as to provide an air-tight space therebetween.

22 Claims, 8 Drawing Sheets

PROTECTIVE GOGGLES

CROSS REFERENCE TO RELATED APPLICATION

This application is a continuation in part of Ser. No. 08/645,017, filed May 9, 1996, now abandoned.

FIELD AND BACKGROUND OF THE INVENTION

The present invention is in the field of eye protection and is concerned with multi-function protection goggles.

Protection of a person's eyes is required at different circumstances and at different environments, e.g. protection against wind, dust, glare of visible light, ultraviolet radiation, laser radiation, shrapnel and other energized fragments, etc.

Heretofore a variety of protective goggles have been proposed. However, such goggles are typically designed for one or two specific purposes and do not provide suitable protection against other hazardous factors.

Another drawback of known goggles concerns the filtering means associated with the venting ports, adapted for ventilation of the space between the wearer's face and the shield. Hitherto filtering means typically comprise a filtering element, such as a fine mesh net, for trapping dust particles. However, such filtering means should be occasionally replaced or removed for cleaning which at times is a complicated process.

For preventing vapor from accumulating on the inner face of the shield, it is known to provide the goggles with venting ports. However, typical venting ports do not prevent fine dust particles from penetrating into the confined space between the wearer's face and the shield, again forming a serious visualizing disturbance and even more so, causing irritation to the wearer.

Still another drawback of the typical goggles is that they interfere with wearing a head cover, e.g. a hat or a helmet and removing the goggles without prior removal of the head cover is impossible or inconvenient.

It is the object of the present invention to provide novel goggles in which the above-referred to disadvantages are significantly reduced or overcome.

SUMMARY OF THE INVENTION

According to the present invention there is provided protective goggles of the type consisting of a rigid, ballistically resistant transparent shield sealingly fittable over the eyes of a wearer via a resilient gasket by means of a head gear, said gasket having airing ports; characterized in that said goggles further comprise a second transparent radiation protective shield detachably retained exterior to said ballistically resistant shield and in substantially parallel relation thereto, impervious sealing means being provided between said ballistically resistant shield and said second shield along their peripheries so as to provide an air-tight space therebetween. Preferably, the goggles comprise a substantially rigid frame intermediate said ballistically resistant shield and said gasket and adapted to support them, said frame being also adapted to detachably retain said second shield.

By a preferred embodiment of the present invention, said frame is adapted to retain said second shield. By a specific application, the second shield is detachably retained to the frame by a pair of prongs projecting from an inner face of the second shield at each end thereof, each prong having an end suitable for engaging within a recess formed at respective ends of the frame, the prongs being switchable between a projecting position and a folded position.

By still a preferred embodiment the frame has an elastic portion at each temple zone so as to allow the shape of the frame to conform with the shape of the wearer's face.

In a specific application of the invention the gasket ha a portion extending between the ballistically resistant shield and the frame with a forward projection forming said impervious sealing means.

Preferably, the goggles also comprise an internal rigid bridging member between a nose portion of the frame and a forehead portion thereof, for reinforcing the frame and for supporting a corrective lens frame positioned between the ballistically resistant shield and the wearer's face.

The second shield used in conjunction with the goggles according to the present invention is adapted to filter out laser radiation within a desired wavelength or to filter out visible radiation within a desired wavelength, or both. Furthermore, both the ballistically resistant shield and the second shield are adapted to filter out ultraviolet radiation.

In still a preferred embodiment of the invention said airing ports comprises labyrinthine grooves formed in the frame at portions bordering between the frame and the resilient gasket, there being suitable openings in the gasket in register with the labyrinthine grooves.

In a specific application of the invention, at least the temple zones of the resilient gasket is an accordion-type seal. Preferably, wherein the gasket comprises airing apertures at inner folds of the gasket, whereby fastening the gasket to the wearer's face entails closing of said airing apertures so as to prevent dust ingress into the space confined between the goggles and the wearer's face.

By a specific application of the invention, the headgear is a head harness suitable for wearing under a hat, a helmet and the like, wherein the head harness consists of a first strap encompassing the back of the head and being releasably attached to a fastening buckle provided on the frame; and a cross-strap attached to the first strap and fitted over the skull. Preferably, the length of the first strap and of the cross-strap is adjustable. Furthermore, excessive end portions of the first strap are attachable to portions of the strap encompassing the back of the head or may be attachable to one another behind the wearer's head, wherein the excessive ends of the first strap are attachable by hook and pile fasteners, referred to as "Velcro™".

The arrangement of the head harness is such that the fastening means enables fastening the first strap by pulling its ends in a direction away from the frame, thus enabling attaching the goggles to the wearer's face by merely pulling the ends of the first strap. However, for removing the goggles from the wearer's face the fastening means should be released, allowing the goggles to be withdrawn from the wearer's face to a suspended position, without the necessity of first removing a hat or helmet from the wearer's head.

BRIEF DESCRIPTION OF THE DRAWINGS

For better understanding, the invention will now be described by way of example only, with reference to their accompanying drawings, in which.

DETAILED DESCRIPTION OF A SPECIFIC EMBODIMENT

Figure 1:
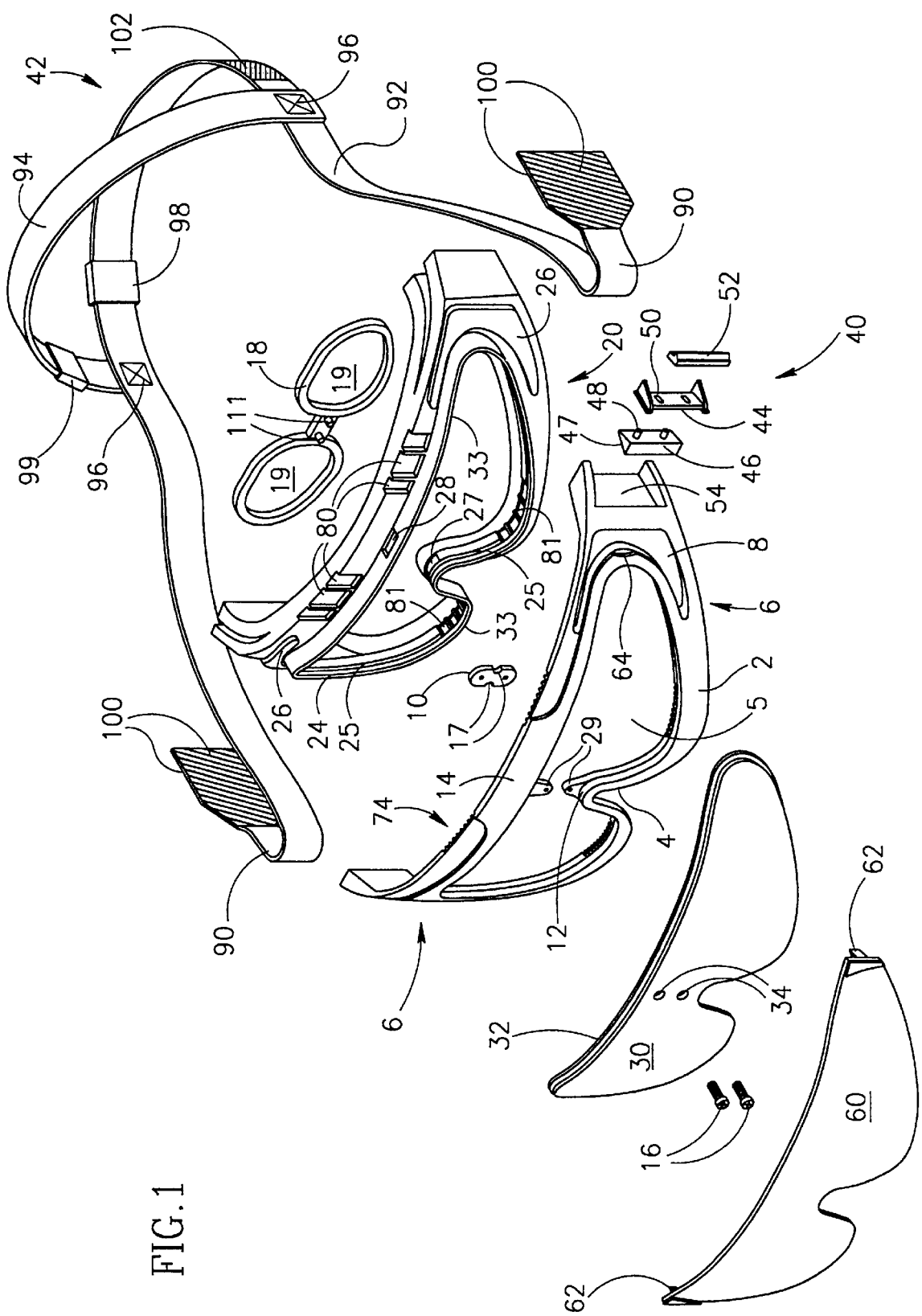
FIG. 1 is an exploded, isometric view of the goggles according to the invention.
Figure 2:
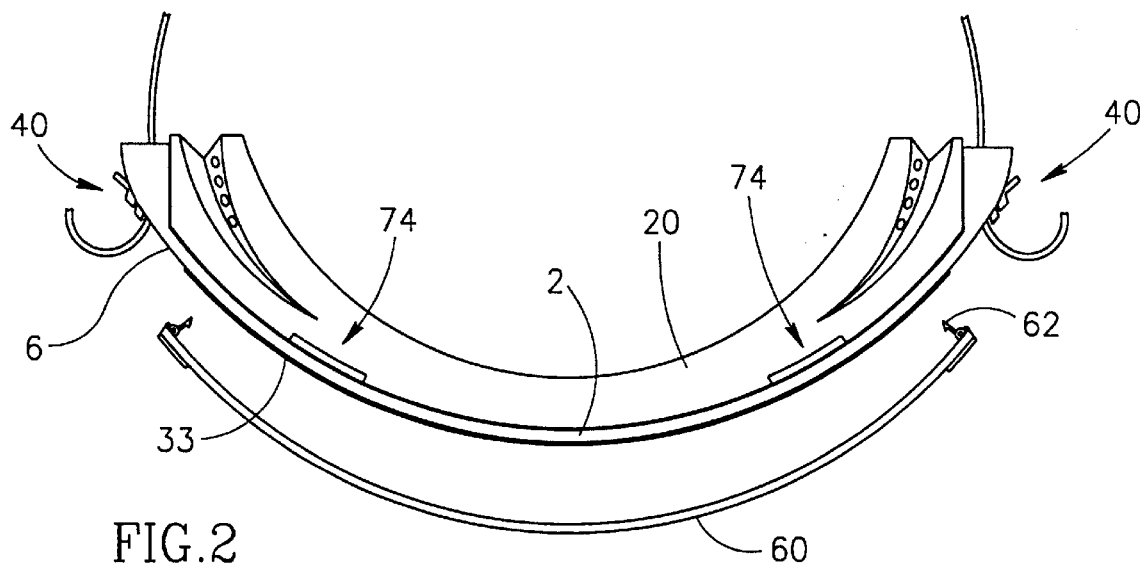
FIG. 2 is a top view of the goggles according to the invention with a second shield in position prior to assembling.
Figure 6:
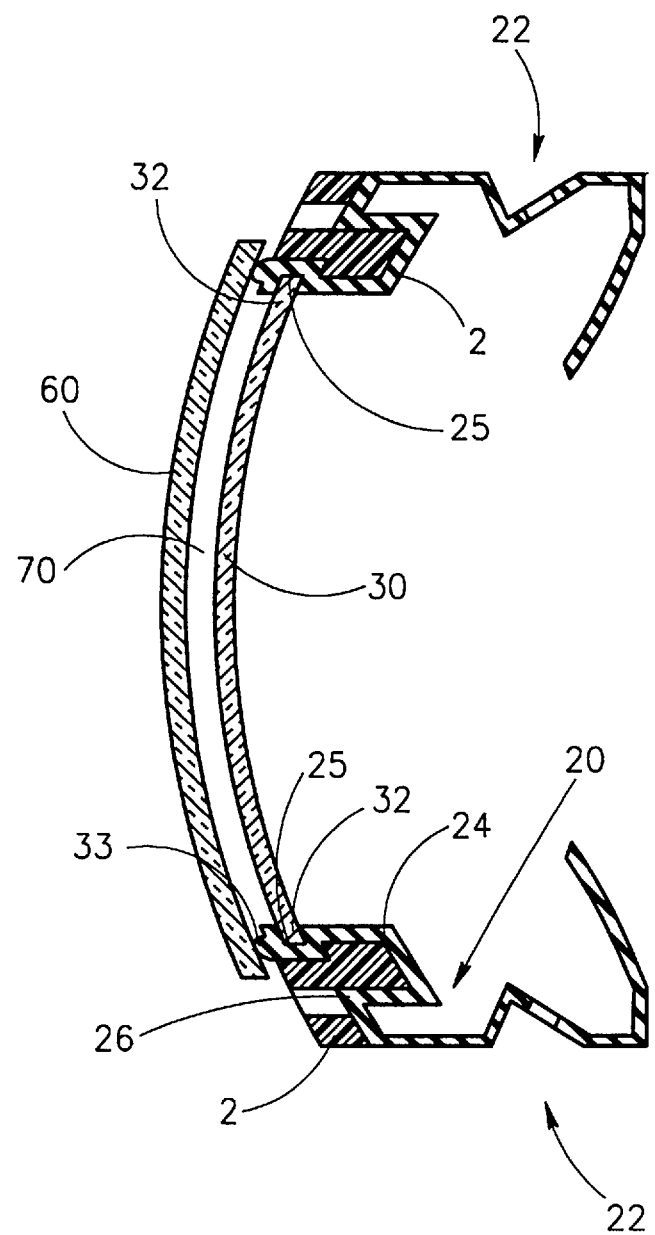
FIG. 6 is a cross-section of the goggles along line VI—VI in FIG. 5A.

Attention is first directed to FIGS. 1, 2 and 6 of the drawings showing a frame 2 having a shape suitable for covering the eyes of a person and comprising a nose bridge portion 4 fittable over the wearer's nose and an opening 5 for receiving a shield. The frame is made of plastic material e.g. Nylon™, and has a cross-section which renders it rigidity. However, the frame 2 comprises at each of the temple zones 6 (corresponding with the wearer's temples), a recess 8 which renders the temple zones some flexibility while maintaining the area around the opening 5 rigid, for the reason which will hereinafter be explained.

The frame 2 also comprises a rigid bridging member 10 between the nose bridge portion 4 and the forehead portion 14. The bridging member 10 is fastened to the frame 2 by a pair of screws 16 and has an indention 17 at each side thereof for maintaining a frame 18 holding corrective lenses 19 as will hereinafter be explained.

A resilient gasket generally designated 20 has a shape conforming both with the frame 2 and with a wearer's face. As can better be seen in FIG. 6, the resilient gasket 20 has an accordion-type sealing portion 22 sealingly fittable over the wearer's face, and a projecting portion 24 extending into the opening 5 of the frame 2 with an internal groove 25. The gasket 20 has also a curved projection 26 (seen in FIG. 1) at each temple zone fittable within the recesses 8 of the frame 2.

Gasket 20 further comprises at the projecting portion 24 two apertures 27 and 28 for receiving corresponding tongues 29 of the frame 2, extending at the nose portion, for attaching the bridging member 10, as explained above.

A transparent shield 30 has essentially the shape of opening 5 of the frame 2 and has a rim 32 for snugly fitting into groove 25 of the projecting portion 24 of the gasket 2, whereby the projecting portion 24 is actually clamped between the shield 30 and the frame 2. The projecting portion 24 has a rim 33 projecting forward and encircling the shield 30. The shield 30 is fixed in position by the screws 16 extending through holes 34 in the shield.

The transparent shield is ballistically-resistant and is adapted for filtering out ultra violet radiation.

At each end of the frame 2 there is a fastener 40 for attaching and adjusting a headgear 42 to the goggles. The fastener consists of a retaining member 44 attached to the frame 2 for example by adhering, sonic welding etc., leaving a gap between the frame and the retaining member, and a wedge-like slide 46 slidable within the gap and having a knurled surface 47 facing the frame 2, and two projections 48 slidingly extending through recesses 50 at the retaining member 44, the projections being attached to an actuator 52, whereby sliding the actuator 52 entails corresponding displacement of the wedge-like slide 46.

The recesses 50 enable displacement of the wedge-like slide between a rearward position in which it bears against a flat surface 54 of the frame and a forward position in which there is a gap between the surface 54 and the slide 46. By another option (not shown), the retaining member 44 may be integrally formed with the frame 2, in which case the actuator 52 is formed with projections slidingly penetrating through openings 50 and attached to the retaining member. The manner in which the head gear 42 is used in conjunction with the goggles will hereinafter be explained in more detail.

Figures 3A, 3B:
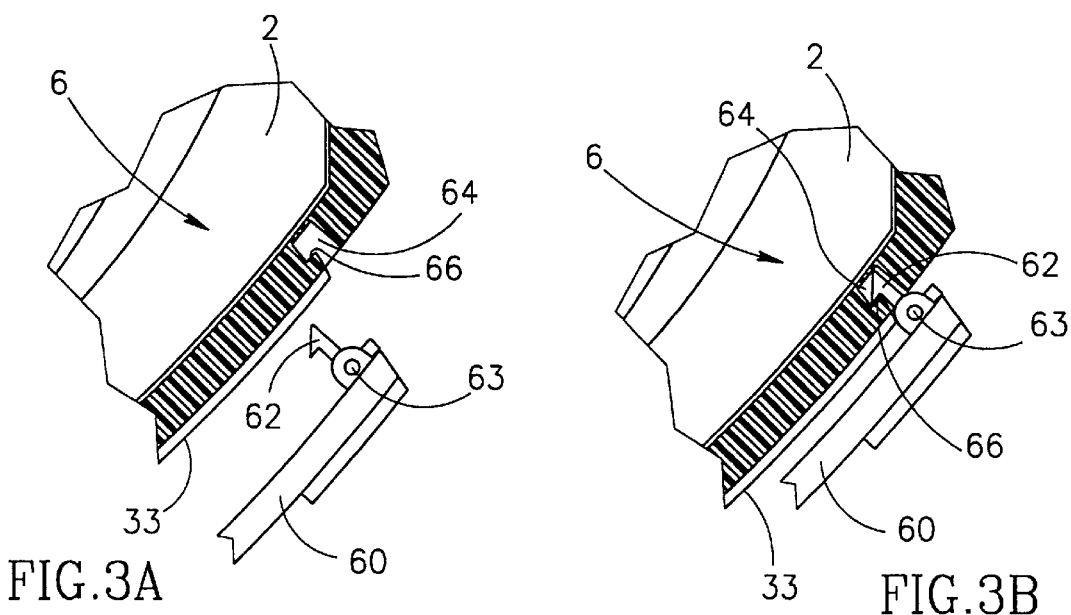
FIGS. 3A and 3B are sections of the temple zone of the goggles before and after assembling the second shield, respectively.
Figure 4:
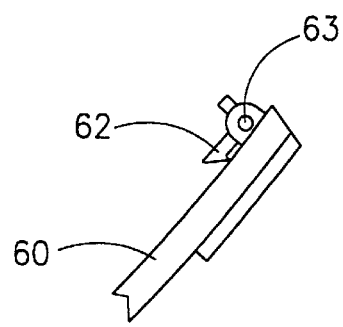
FIG. 4 is an end portion of the second shield used in conjunction with the goggles according to the present invention, the prongs in their folded position.

As can better be seen in FIGS. 2 to 4, a second shield 60 is attachable to the frame 2, the second shield being essentially transparent and is adapted to filter out laser radiation within a desired wavelength range and/or to filter out visible radiation within a desired wavelength range. Preferably the second shield 60 filters out also ultra violet radiation.

The second shield 60 is slightly larger than the first shield 30 and comprises at each end thereof a hook-shaped prong 62 projecting from an inner face of the shield 60, the prongs 62 are hinged at 63 to the second shield and are switchable between a projecting position (as seen in FIGS. 2 and 3) and a collapsed position (as seen in FIG. 4), the collapsed position useful for protecting the prongs from breakage while not in use.

As seen in FIGS. 3A and 3B, the frame 2 has at each temple zone 6 a recess 64 with an inner retaining shoulder 66. For attaching the second shield 60 to the frame 2, the prongs 62 are switched into their projecting position and are pressed into the recesses 64, whereby the hooked end of the prongs snappingly engages with the shoulder 66 of the recess in 64, as seen in FIG. 3B.

For detaching the second shield 60 from the frame 2, light pressure is applied on the central portion of the second shield and then the end portions of the second shield may be pulled, extracting the prongs 62 from the retaining shoulders 66.

The arrangement is such that when the second shield 60 is assembled to the goggles, it bears at its circumference against the rim 33 of the gasket 20, thereby forming an essentially air-tight space between the parallel disposed shields 30 and 60, as seen in FIGS. 5 and 6. This arrangement ensures that dust and vapor do not collect between the shields. Furthermore, this arrangement provides improved thermal isolation of the first shield 30 from the surroundings, thereby preventing accumulating of vapor on the inner face of the first shield.

Figure 7:
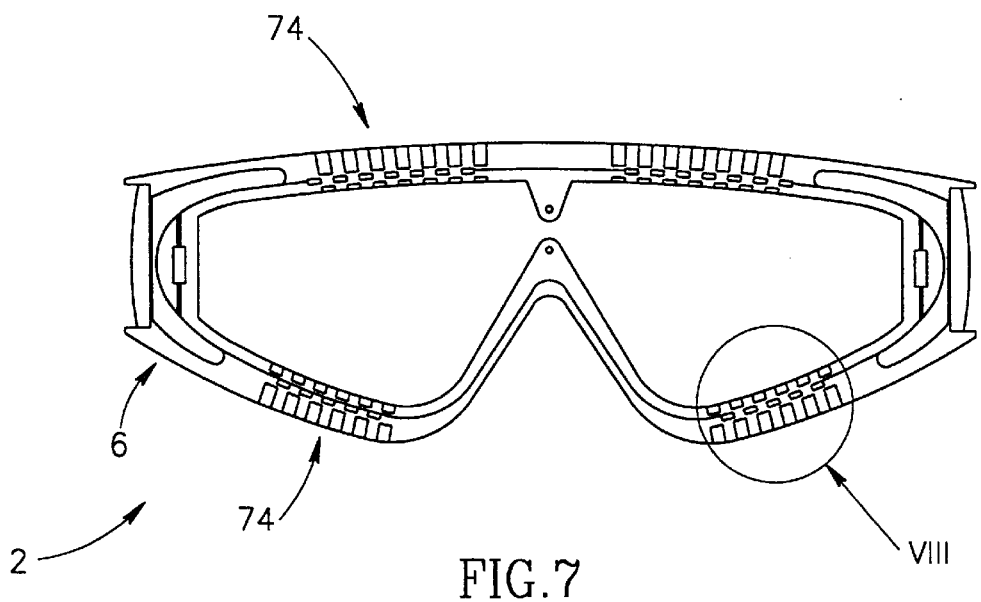
FIG. 7 is a rear (inner) view of the goggles with the resilient gasket removed, illustrating a first type of airing ports.
Figure 8A:
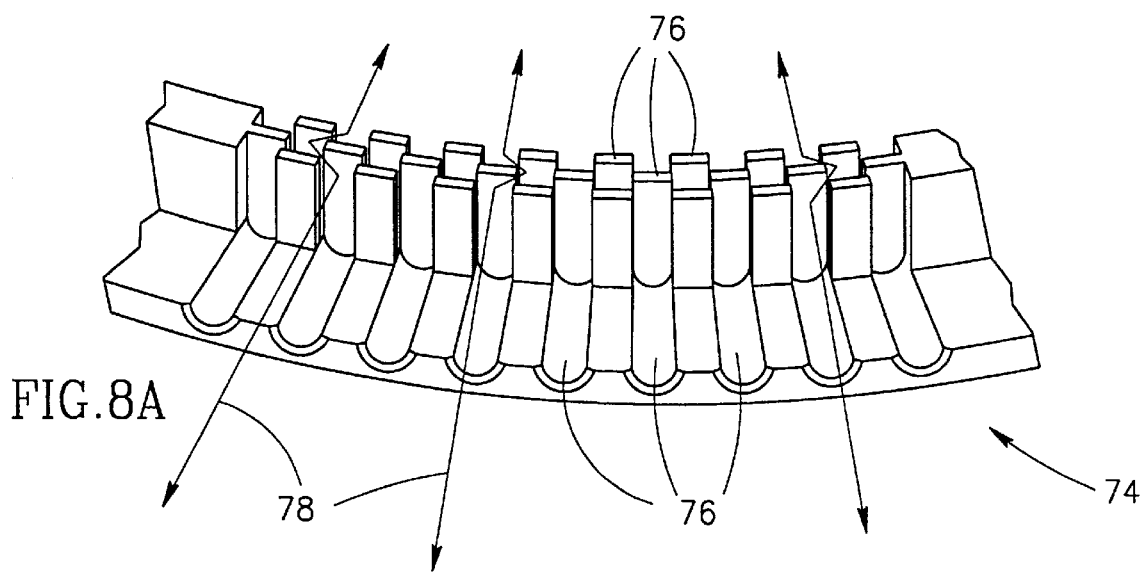
FIGS. 8A and 8B are enlarged isometric and planner views of portion VIII in FIG. 7, respectively.
Figure 8B:
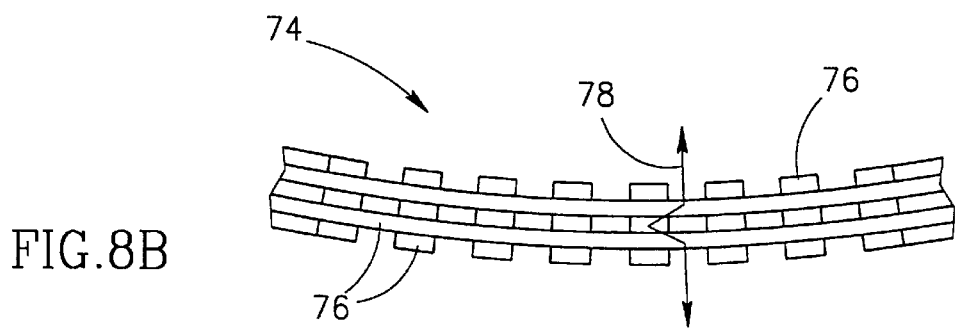

Further references now made also to FIGS. 7 and 8 illustrating a first type of airing ports wherein the frame 2 comprises four airing ports generally designated 74, each being of the labyrinthine-type and constructed of a plurality of protuberances 76 arranged so as to form labyrinthine at grooves 78 extending the widths of the frame so as to enable air venting on the one hand and on the other to prevent ingress of dust and scattering liquids. As seen in FIGS. 1, 2 and 5 of the drawings, the gasket 20 comprises indentions 80 at the forehead portion and openings 81 at lower portions, in register with the labyrinth sign grooves 78, for allowing air passage therethrough.

Figure 5A:
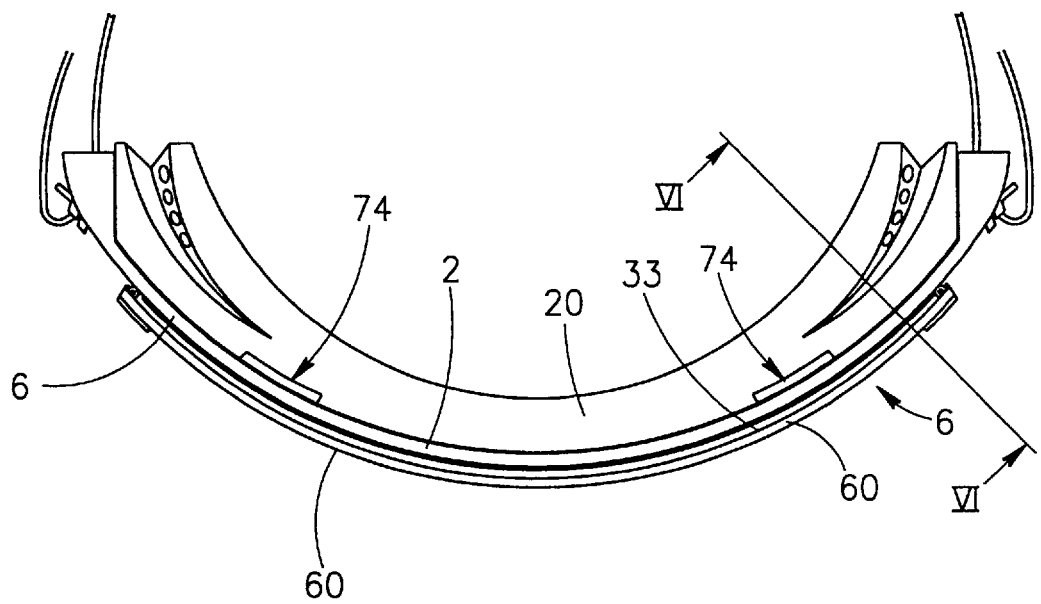
FIGS. 5A and 5B are top views of the goggles according to the invention in a non-fastened and in a fastened positions, respectively.
Figure 5B:
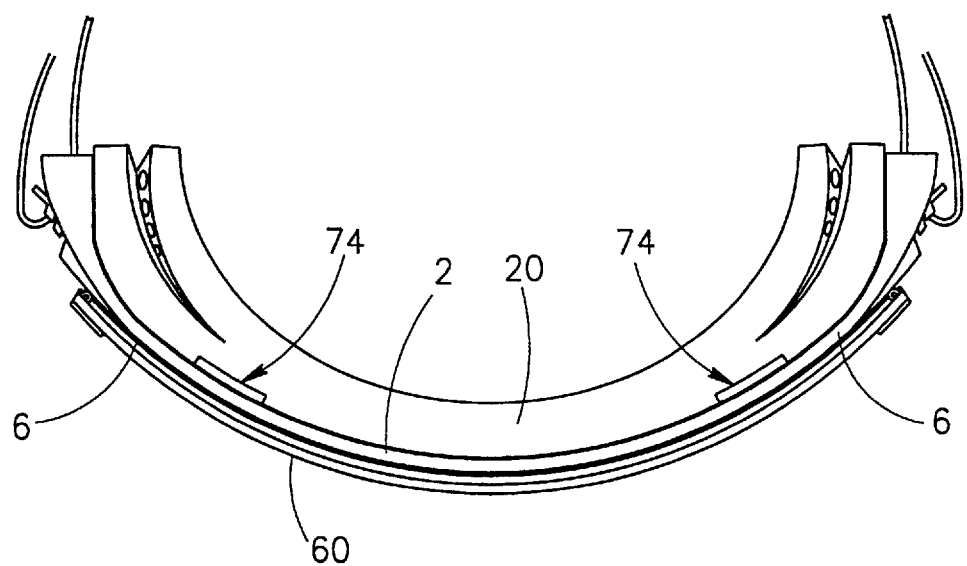

Attention is now directed to FIGS. 1, 5A and 5B. As previously explained, each of the temple zones 6 of the frame 2 comprises a recess 8 rendering the frame flexibility owing to decreasing of the cross-section area of the frame 2 at those zones.

This arrangement makes the goggles suitable for use by wearers having different face sizes, wherein FIG. 5A illustrates the goggles in a non-deflected position suitable for wearing over an essentially wide face, whereas FIG. 5B illustrates the goggles in the deflected position, suitable for wearing over an essentially narrow face. It should obvious that the resilient gasket 20 conforms the shape of the frame 2 and provides adequate sealing between the wearer's face and the goggles, with the rate of fastening the headgear 42 effecting the imperviousness of the goggles.

Figure 9A:
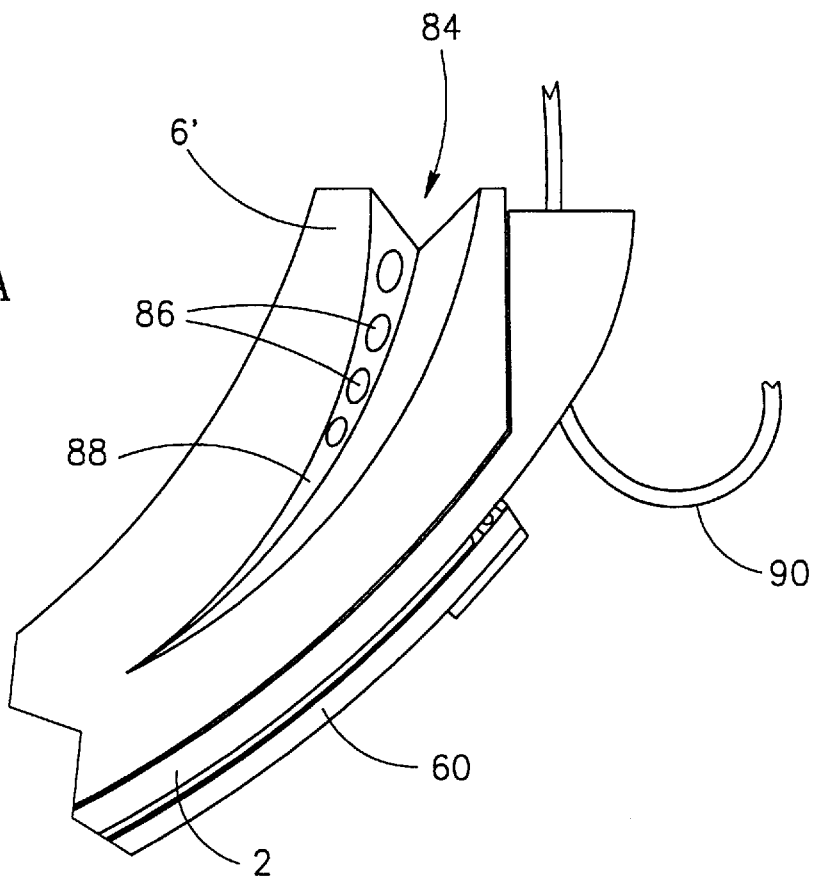
FIGS. 9A and 9B are end portions of the goggles in enlarged scale, illustrating a second type of airing ports, in an airing position and in a sealed position, respectively.
Figure 9B:
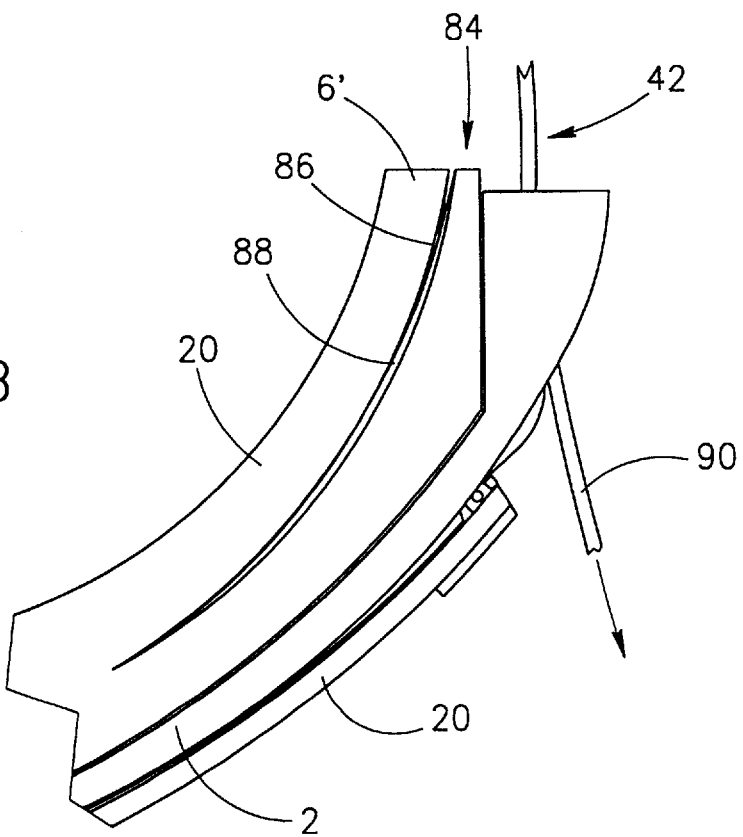

FIGS. 9A and 9B illustrate a second type of airing ports generally referred to as 84, wherein a plurality of apertures 86 are formed at an inner fold 88 of a temple portion 6' of the gaskets 20. The arrangement is such that in normal conditions of use, the apertures 86 are kept open, enabling improved airing of the inner space between the wearers face and the goggles. However, in dusty environments the goggles are fastened to the wearer's face by fastening the end portions 90 of the headgear 42, entailing covering of the holes 86 by overlapping folds of the accordion-type gasket. It should however be obvious that the apertures may be formed at any portions of the gasket, preferably at the temple portions.

Figure 10:
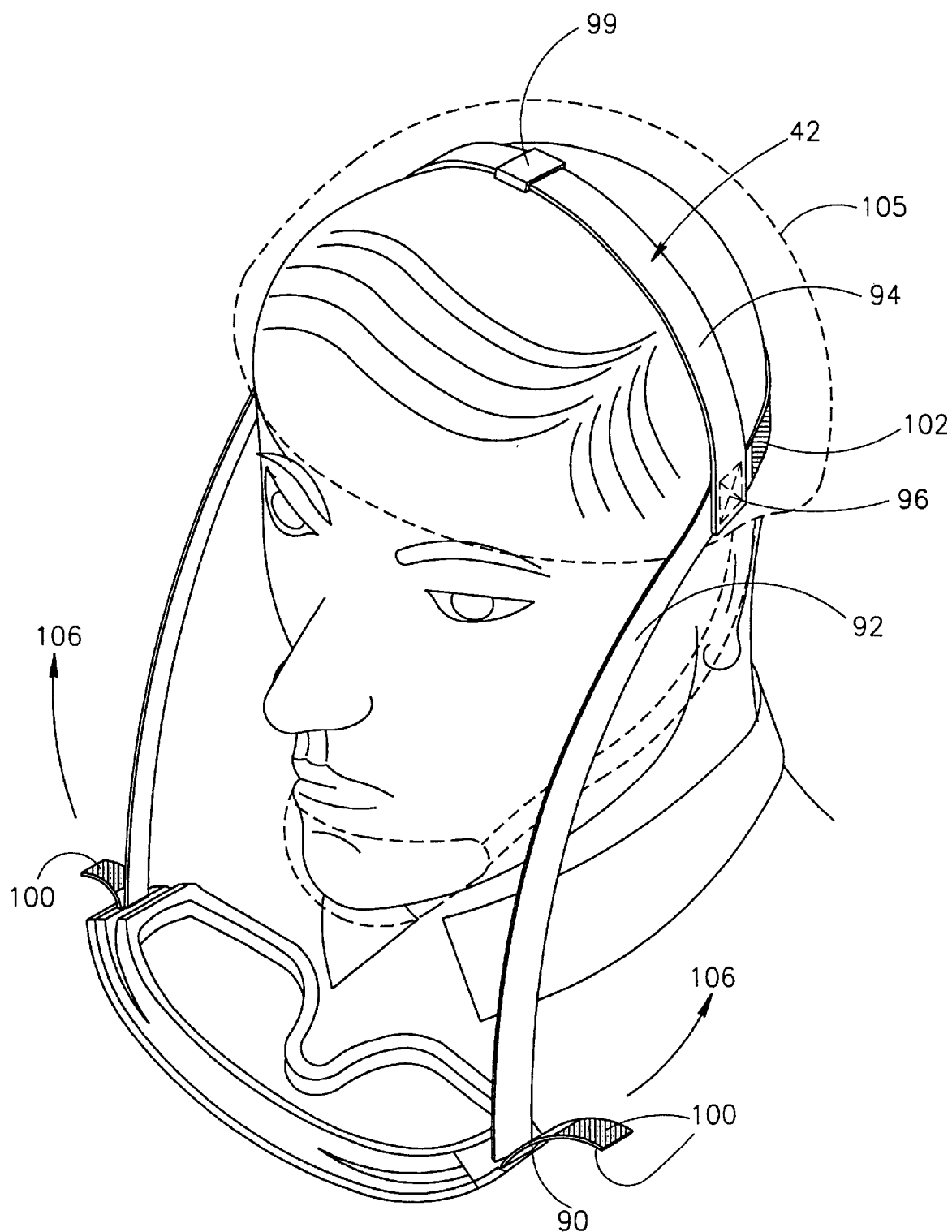
FIG. 10 is an isometric view illustrating the goggles in a suspended position, the wearer wearing a helmet.
Figure 11:
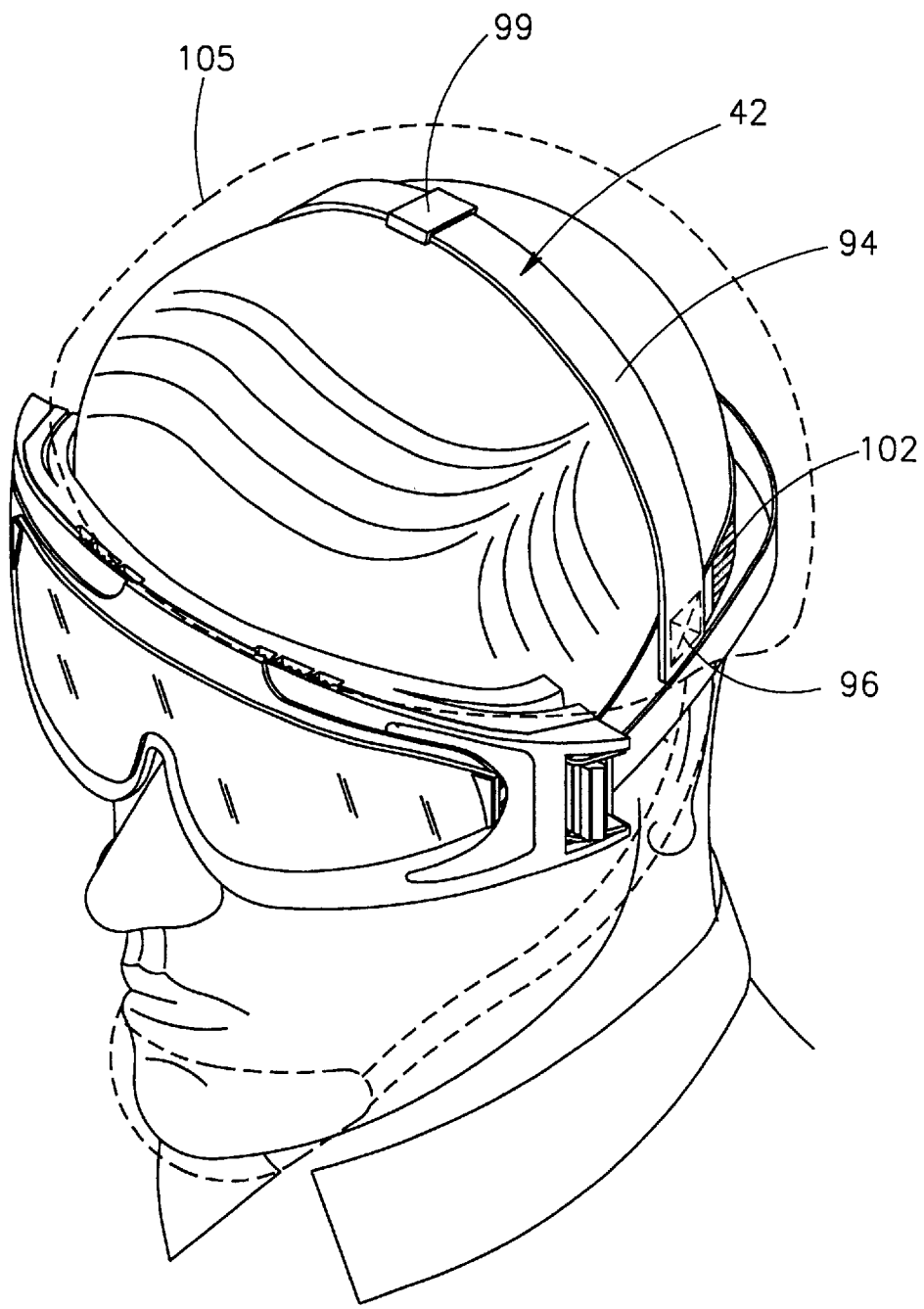
FIG. 11 illustrates the goggles according to the invention attached to the wearer's face with a helmet.

Attention is now directed to FIGS. 1, 10 and 11, wherein the headgear 42 is a head-harness consisting of a first strap 92 designed for encompassing the back of the wearer's head and being long enough so as to allow the goggles to suspend to about the wearer's chest, as seen in FIG. 10. The head harness further comprises a cross-strap 94 attached at 96 to the first strap 92 and fitted over the wearer's skull. Both the first strap 92 and the cross-strap 94 comprise at least one length adjusting buckle 98 and 99, respectively (buckle 98 seen only in FIG. 1), so as to allow adjustment of the straps to the size of the wearer's head.

The end portions 90 of the first strap 92 comprise pile and hook fasteners 100 (known as "Velcro™") at both faces of the strap and two such fastener patches 102 (only one seen).

In FIG. 10, the goggles are seen in a suspended position with the head harness 42 fitted over the skull of a person wearing a helmet 105, with the straps 92 and 94 not interfering with the helmet. For wearing the goggles over the eyes, the end portions 90 of the first strap 92 are pulled away from the goggles in direction of arrows 106 whereby owing to friction between the knurled surface 47 and the first straps 92, the wedge-like slide 46 is displaced forward (i.e, in a direction away from the wearer), thus increasing the gap and allowing adjusting the length of straps. However, upon release of the end portions 90, the wedge-like slide 46 returns to its original position (rear position), whereby the strap is clamped between the slide 46 and the flat surface 54 of the frame. Then the excessive portions of the first strap are fastened to one another over the helmet, as illustrated in FIG. 11. However, when the headgear is used not under a helmet the excessive end portions are fastened to the patches 102.

For releasing the goggles, the actuator 52 of the fastener 40 is manually pushed forward (in a direction away from the wearer's face), thus increasing the gap between the slide 46 and the flat surface 54 of the frame 2, whereby the straps are free to move within the gap and the goggles may be removed from the wearer's face, while shortening the excessive length of the free ends of the first strap.

Reference is made back to FIG. I in which it is seen that the frame 18 holding the corrective lenses 19 further comprises two forward projecting studs 111 adapted for snap fitting into recesses 17 of the bridging member 10, whereby a person requiring corrective lenses may comfortably use the goggles after removing his spectacles.

We claim:

1. Protective goggles comprising a rigid, ballistically resistant transparent shield sealingly fittable over the eyes of a wearer via a resilient gasket by a head gear, said goggles airing ports; characterized in that said goggles further comprise a second transparent radiation protective shield detachably retained exterior to said ballistically resistant shield and in substantially parallel relation thereto, impervious sealing means being provided between said ballistically resistant shield and said second shield along their peripheries so as to provide an air-tight space therebetween; and a substantially rigid frame intermediate said ballistically resistant shield and said gasket and adapted to support them.

2. Protective goggles according to claim 1, wherein said frame is adapted to detachably retain said second shield.

3. Protective goggles according to claim 2, wherein the second shield is detachably retained to the frame by a pair of prongs projecting from an inner face of the second shield at each end thereof, each prong having an end suitable for engaging within a recess formed at respective ends of the frame.

4. Protective goggles according to claim 3, wherein the prongs are switchable between a projecting position and a folded position.

5. Protective goggles according to claim 2, wherein the frame has an elastic portion at each temple zone so as to conform to the wearer's face.

6. Protective goggles according to claim 2, wherein the gasket has a portion extending between the ballistically resistant shield and the frame with a forward projection forming said impervious sealing means.

7. Protective goggles according to claim 1, further comprising an internal rigid bridging member between a nose portion of the frame and a forehead portion thereof.

8. Protective goggles according to claim 7, wherein the bridging member is adapted to support a corrective lens frame between the ballistically resistant shield and the wearer's face.

9. Protective goggles according to claim 1, wherein the second shield is adapted to filter out laser radiation within a desired wavelength range.

10. Protective goggles according to claim 1, wherein the second shield is adapted to filter out visible radiation within a desired wavelength range.

11. Protective goggles according to claim 1, wherein at least one of the ballistically resistant shield and the second shield is adapted to filter out ultraviolet radiation.

12. Protective goggles according to claim 1, wherein at least the temple zones of the resilient seal is an accordion-type gasket.

13. Protective goggles according to claim 12, wherein the gasket comprises airing ports at inner folds of the gasket, whereby fastening the gasket to the wearer's face entails closing of said airing ports so as to prevent dust ingress into the space confined between the goggles and the wearer's face.

14. Protective goggles according to claim 1, wherein said airing ports comprises labyrinthine grooves formed in the frame at portions bordering between the frame and the gasket, there being suitable openings in the gasket in register with the labyrinthine grooves.

15. Protective goggles according to claim 1, wherein the head gear is a head harness suitable for wearing under headwear or headgear.

16. Protective goggles according to claim 15, wherein the head harness comprises a first strap encompassing the back of the head and being releasably attached to fastening means provided on the frame; and a cross-strap attached to the first strap and fitted over the skull.

17. Protective goggles according to claim 16, wherein the length of the first strap is adjustable.

18. Protective goggles according to claim 16, wherein excessive end-portions of the first strap are attachable to the portions of the strap encompassing the back of the head.

19. Protective goggles according to claim 16, wherein excessive end-portions of the first strap are attachable to one another behind the wearer's head.

20. Protective goggles according to claim 16, wherein excessive ends of the first strap are attachable by hook and pile fasteners.

21. Protective goggles according to claim 16, wherein the length of the cross-strap is adjustable.

22. Protective goggles according to claim 16, wherein the fastening means enables fastening the first strap by pulling its ends in a direction away from the frame, whereas for releasing the first strap the fastening means should be released.

* * * * *

UNITED STATES PATENT AND TRADEMARK OFFICE
CERTIFICATE OF CORRECTION

PATENT NO. : 5,802,622
DATED : Sep. 8, 1998
INVENTOR(S) : Baharad et al.

It is certified that error appears in the above-identified patent and that said Letters Patent is hereby corrected as shown below:

Column 6, line 12 (Claim 1), after "goggles" insert therefor -- having --.

Signed and Sealed this

Eleventh Day of May, 1999

Q. TODD DICKINSON

Attest:

Attesting Officer

Acting Commissioner of Patents and Trademarks